(12) United States Patent
Steadman Booker et al.

(10) Patent No.: US 11,307,312 B2
(45) Date of Patent: Apr. 19, 2022

(54) IMAGE ACQUISITION

(71) Applicant: KONINKLIJKE PHILIPS N.V., Eindhoven (NL)

(72) Inventors: Roger Steadman Booker, Aachen (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 38 days.

(21) Appl. No.: 16/978,855

(22) PCT Filed: Feb. 25, 2019

(86) PCT No.: PCT/EP2019/054501
§ 371 (c)(1),
(2) Date: Sep. 8, 2020

(87) PCT Pub. No.: WO2019/170441
PCT Pub. Date: Sep. 12, 2019

(65) Prior Publication Data
US 2021/0041580 A1    Feb. 11, 2021

(30) Foreign Application Priority Data

Mar. 7, 2018   (EP) .................... 18160442

(51) Int. Cl.
*G01T 1/17*   (2006.01)
*G01T 1/20*   (2006.01)
(Continued)

(52) U.S. Cl.
CPC .............. *G01T 1/17* (2013.01); *A61B 6/4208* (2013.01); *G01T 1/20184* (2020.05);
(Continued)

(58) Field of Classification Search
CPC ..... G01T 1/17; G01T 1/20184; G01T 1/2985; A61B 6/4208; A61B 6/032; A61B 6/4035; A61B 6/54
See application file for complete search history.

(56) References Cited

U.S. PATENT DOCUMENTS 7,139,367 B1 * 11/2006 Le ..................... G01V 5/0008
378/98
8,735,832 B2   5/2014 Chappo
(Continued)

FOREIGN PATENT DOCUMENTS

WO   2009156927 A2   12/2009

OTHER PUBLICATIONS

International Search Report and Written Opinion of PCT/2019/054501, dated Apr. 30, 2019.
(Continued)

*Primary Examiner* — Marcus H Taningco
(74) *Attorney, Agent, or Firm* — Larry Liberchuk

(57) ABSTRACT

The present invention relates to a detection device for X-rays, an imaging system and a method for detecting electro-magnetic radiation using a detection device for X-rays, wherein an estimate of an incomplete measurement is acquired prior to a discontinuity of the electromagnetic radiation, wherein the discontinuity is a change or interruption in a beam or in an intensity of the electromagnetic radiation.

11 Claims, 5 Drawing Sheets

(51) Int. Cl.
  *A61B 6/00* (2006.01)
  *G01T 1/29* (2006.01)
  *A61B 6/03* (2006.01)

(52) U.S. Cl.
  CPC ............ *G01T 1/2985* (2013.01); *A61B 6/032* (2013.01); *A61B 6/4035* (2013.01)

(56) References Cited

U.S. PATENT DOCUMENTS

| | | | |
|---|---|---|---|
| 9,304,210 B2 * | 4/2016 | Yoon | G01T 1/17 |
| 2011/0085043 A1 * | 4/2011 | Kamiyama | H04N 5/332 |
| | | | 348/164 |
| 2011/0216878 A1 | 9/2011 | Roessl | |
| 2011/0291019 A1 | 12/2011 | Yuan | |
| 2015/0085985 A1 * | 3/2015 | Funaki | H04N 5/378 |
| | | | 378/98 |
| 2015/0350584 A1 | 12/2015 | Fenigstein | |
| 2016/0363674 A1 | 12/2016 | Jacob | |

OTHER PUBLICATIONS

Roessl, Ewald et al "Dual-Energy X-Ray Imaging by Simultaneous Integration and Campbelling Readout", Nuclear Science Symposium Conference Record, Nov. 19, 2010, pp. 2112-2115.

* cited by examiner

IMAGE ACQUISITION

FIELD OF THE INVENTION

The present invention relates to a detection device for X-rays, an according imaging system, a method for detecting electromagnetic radiation using the detection device for X-rays, a computer program element and a computer readable medium.

BACKGROUND OF THE INVENTION

The advent of new Computed Tomography (CT) image acquisition methods, e.g. Sparse sampling with Grid Switch tubes, kVp switching (kVp is a common notation for tube acceleration voltage) or grid filters, require that the readout electronics do not propagate signal information across a distinct discontinuity of the X-ray intensity which can happen either by a change of spectrum or blank period of an X-ray tube.

A known readout topology is that of a CT readout ASIC comprising a current to frequency converter or ratiometric converter or folded integration converter, allowing to achieve a large dynamic range and resolution. It however inherently can entail a certain amount of error in signal quantification in the event of e.g. X-ray being shut off for a short period of time. Furthermore, other methods to adapt the readout architecture may also be exploited to gain additional spectral information by estimating the variance of the signal. Such a method is also known as Campbell readout. However, these methods do not consider distinct discontinuities.

SUMMARY OF THE INVENTION

There may thus be a need to improve CT image acquisition methods.

The object of the present invention is solved by the subject-matter of the independent claims; further embodiments are incorporated in the dependent claims. It should be noted that the following described aspects of the invention apply also for the detection device, the imaging system and the method and vice versa.

An imaging system according to the present invention, such as a CT apparatus for example, comprises a source for providing electromagnetic radiation, such as X-rays, and a detection device therefore. The generated X-rays form an electromagnetic radiation beam. The beam traverses an object of examination, such as a patient. After having traversed the object of examination, the beam is incident on a detection device for X-rays according to the present invention.

According to the present invention, the detection device for X-rays comprises: at least one sensor adapted to provide a current in response to electromagnetic radiation exposure during at least one image acquisition frame; at least one electronics board comprising at least one integrator providing a capacitor, that is configured to discharge in response to the current provided by the sensor, wherein a discharge of the capacitor defines at least one cycle; a capacitor discharge analyzer, a counter and a processor unit. The capacitor discharge analyzer is configured to analyze the discharge of the capacitor and to provide a full-discharge signal when the capacitor is fully discharged in response to the current provided by the sensor. The counter is configured to measure a cycle time, defined as a period between a start of a new cycle and a full discharge of the capacitor based on the full-discharge signal provided to the counter by the capacitor discharge analyzer. The processor unit is configured to: obtain the cycle time of the at least one cycle from the counter; store the provided cycle time of the at least one cycle; and comparing the cycle time of the at least one cycle by comparison with one or more previously stored cycle time(s). An estimate of an incomplete cycle is acquired prior to a discontinuity of the electromagnetic radiation, wherein the discontinuity is a change or interruption in a beam of the electromagnetic radiation or in an intensity of the electromagnetic radiation.

The detection device for X-rays comprises at least one sensor for sensing incident electromagnetic radiation after having traversed the object of examination during at least one image acquisition frame. The image acquisition frame is defined as time interval during which the object of examination is exposed to electromagnetic radiation. The image acquisition frame can be defined as a time interval comprising a predefined number of cycles. The number of cycles may vary according to the image acquisition method used and/or according to the employed electronics board. Furthermore, a discontinuity during an image acquisition frame may indicate a termination thereof followed by a subsequent image acquisition frame. The object can be exposed to the electromagnetic radiation during subsequent image acquisition frames.

The one or more sensor(s) provides a current in response to the electromagnetic radiation exposure. It should be noted, that the invention comprises any current direction provided by the sensor(s), which comprises any suited sensor type.

The current provided by the at least one sensor is provided to an electronics board. The electronic circuit of the electronics board may comprise Analog/Digital (A/D) conversion electronics. The basic circuit of the electronics board comprises a current to frequency converter, wherein the current provided by the sensor is applied to the input of an integrator providing the capacitor which is charged. The integrator output is a voltage ramp with a slope proportional to the input current provided by the sensor. When the integrator output reaches a threshold (which can be defined) a present amount of charge of the capacitor is discharged. The capacitor is discharged in response to the current (and bias) provided by the sensor. The capacitor can be a feedback capacitor. The discharge of the capacitor causes a new cycle in response to the current provided by the sensor. A discharge of the capacitor is referred to as cycle herein. In some examples, the full discharge of the capacitor may define the cycle.

A capacitor discharge analyzer is configured to analyze the discharge of the capacitor and to provide a full-discharge signal when the capacitor is fully discharged in response to the current provided by the sensor. The capacitor discharge analyzer may be configured to receive an input signal form a charge measuring device coupled to the capacitor that is configured to measure the charge of the capacitor over time from an initial capacitor charge to full discharge (zero capacitor charge). The capacitor discharge analyzer may be comprised in a processor unit.

The one or more sensors may comprise an array of photodiodes held on a substrate typically made of ceramic, for example. In some examples, the photodiode can be equipped with a scintillator for the X-ray to optical conversion.

The time it takes to fully discharge the amount of charge present in the capacitor is herein referred to as cycle time. The cycle time is indicative of the intensity of the electromagnetic radiation.

The at least one cycle time is stored, e.g. in a storage element related to a or the processor unit. The cycle time(s) for one or all cycles can be acquired and stored in the storage element. It should be noted, that discharging the capacitor usually also (implicitly) specifies a current direction, this invention comprises any current direction.

The cycle time of the at least one cycle is compared with one or more previously stored cycle time(s). A default value may be stored as cycle time before the first discharge of the capacitor, i.e. before the first cycle time can be provided. The default value is then replaced by this first cycle time.

In case of a discontinuity of the electromagnetic radiation, wherein the discontinuity is a change or interruption in the electromagnetic radiation beam or in an intensity of the electromagnetic radiation, an estimate of an according incomplete cycle is acquired. The discontinuity can be caused by a grid-switch, a change in the impinging spectrum, a switch-off, etc. In other words, if a cycle is interrupted before its completion, i.e. the elapsed time of the incomplete cycle is less than the cycle time for the last completed cycle, the ratio of both cycle times represents an estimate of the incomplete cycle before the discontinuity of the beam. The incomplete cycle can also be referred to as residual signal. By providing the estimate of the incomplete cycle, this cycle is taken into account, e.g. by correcting the output of the detection device, for the corresponding image acquisition frame. The evaluation of the cycle time after a discontinuity allows eliminating crosstalk across adjacent image acquisition frames or projections.

According to the present invention, the imaging system comprising a source for providing electromagnetic radiation and the detection device provides an estimate of an incomplete cycle acquired prior to a discontinuity of the electromagnetic radiation, wherein the discontinuity is a change or interruption in a beam of the electromagnetic radiation or in an intensity of the electromagnetic radiation.

According to the present invention, a method for detecting electromagnetic radiation using a detection device for X-rays comprises the following steps: sensing electromagnetic radiation exposure during at least one image acquisition frame; providing a cycle time of at least one cycle, wherein the cycle time is defined as the period to fully discharge a capacitor of at least one integrator of an electronics board of the detection device; storing the provided cycle time of the at least one cycle; and comparing the cycle time of the at least one cycle with one or more previously stored cycle time(s), wherein an estimate of an incomplete cycle is acquired prior to a discontinuity of the electromagnetic radiation, wherein the discontinuity is a change or interruption in a beam of the electromagnetic radiation or in an intensity of the electromagnetic radiation.

According to an example, the cycle time of the at least one cycle replaces the stored cycle time of a last completed cycle, if the at least one cycle is complete. A previous stored cycle time is updated/replaced by the cycle time of the actual cycle, if the latter is fully completed. A default value as cycle time may be provided before the first cycle time can be provided. The default value is then replaced by the first cycle time. Thus, the cycle time of the last full cycle is continuously acquired and updated. At the end of each cycle, the cycle time is stored for a fully completed cycle and the cycle time for the next cycle of the image acquisition frame is provided. If this next cycle is fully completed, the previously stored cycle time is replaced by the actual cycle time, i.e. at any given time only one elapsed time measurement is stored.

According to an example, the estimate for the incomplete cycle is acquired for a cycle time which is less than the stored cycle time of the last completed cycle. The time elapsed before the discontinuity is compared to the cycle time stored for the last completed cycle. In this example only the last completed cycle time is made available for comparison with the provided cycle time of the actual cycle.

According to an example, the ratio of the provided cycle time and the cycle time for the last completed cycle represents an estimate of the incomplete cycle. The ratio between both cycle times represents an estimate of the incomplete cycle before the discontinuity of the beam.

According to an example, the cycle times of all cycles during at least one image acquisition frame are provided and a variance of the cycle time is calculated. The cycle times of all events during the at least one image acquisition frame is used. The variance is calculated, which is the expectation of the squared deviation of a cycle time from the mean of the cycle times. The cycle times are weighted according to the square of the amplitude (this is also known as Campbell-mode readout). The distribution of the cycle time of each cycle during an image acquisition frame is a measure of the variance of the intensity of the X-ray beam within that image acquisition frame. Thus, a second readout channel (or Campbell channel) is provided, which has a different spectral footprint than an integrated mode (integrating capacitor charge). Providing such Campbell-mode readout allows energy separation of the electromagnetic radiation. The variance of the cycle time can be calculated for each cycle per image acquisition frame (or plurality of image acquisition frames).

According to an example, the discontinuity comprises a change of wavelength of the electromagnetic radiation and/or a blank period of the electromagnetic radiation. A blank period of the electromagnetic radiation can be caused for instance by a grid-switch. Such discontinuity would lead to a partial cycle during radiation exposure. This could lead to an erroneous output of the detection device in the event of e.g. a shut-off of the X-ray beam for a short period of time. With the proposed method, an estimate of an incomplete cycle is acquired and the measurements during one or more image acquisition frames are compensated or corrected, and the image acquisition is improved.

Among image acquisition methods the use of a fine-pitch grid in front of the X-ray tube (source) and making use of a focal spot deflection capability might be of interest for some applications. The X-ray beam can then be filtered by the grid or substantially unaltered by the grid. Thus, the beam has a distinct spectral footprint at each position of the focal spot deflection (DFS=Dual Focal Spot). In such grid based image acquisition methods the filtered beam might have a significant change (reduction) in the intensity of the electromagnetic radiation, i.e. there is a discontinuity of the electromagnetic radiation. To compensate for such intensity loss, image acquisition frame-by-frame X-ray dose modulation is possible, however according X-ray tube and the speed requirements must be fulfilled.

According to an example, the discontinuity of the electromagnetic radiation is compensated by modifying a gain of the at least one cycle during the at least one image acquisition frame. Optimal spectral results, e.g. optimized quantum to noise ratio, are obtained by modification of the gain during at least one image acquisition frame. This reduces or eliminates the need to acquire image acquisition frames with different integration periods depending on the DFS position, for example. In other words, such automatic change of gain, which is frame based, can be implemented in any appropriate readout topology. According to an example, the modification of the gain comprises adding a reference voltage which resets the capacitor when the signal reaches a certain threshold. The threshold can be ground, for example. Thus, an effective current to frequency converter (by counting the amount of charge cycles within a frame) is provided.

According to an example, the reference voltage is different for subsequent image acquisition frames. Using a different reference voltage for every image acquisition frame, allows to effectively modify the gain of the front-end readout-electronics. In some examples, the image acquisition frames are numbered, and that odd frames use a reference voltage which is half of the one used for even frames. This leads to a gain for odd frames which is effectively twice the gain of the even frames. In some examples, the ratio between both such reference voltages can be chosen or tuned to operate the detection device in an optimal configuration given by an expected signal intensity variation caused by changes of the tube focal spot (e.g. DFS explained above) in combination with a grid, thereby enhancing the spectral separation across the focal spot positions. Alternately, such a change in intensity may also account for the photon flux caused by kVp-switching.

The present invention can be used for various image acquisition methods and systems such as CT, spectral CT, Grid-based spectral CT, kVp-switching, sparse sampling and the like.

According to the present invention, a computer program element for controlling an apparatus according to the invention is proposed, which, when being executed by a processing unit, is adapted to perform the method steps mentioned above. Also, an according computer readable medium having stored the program element is proposed.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
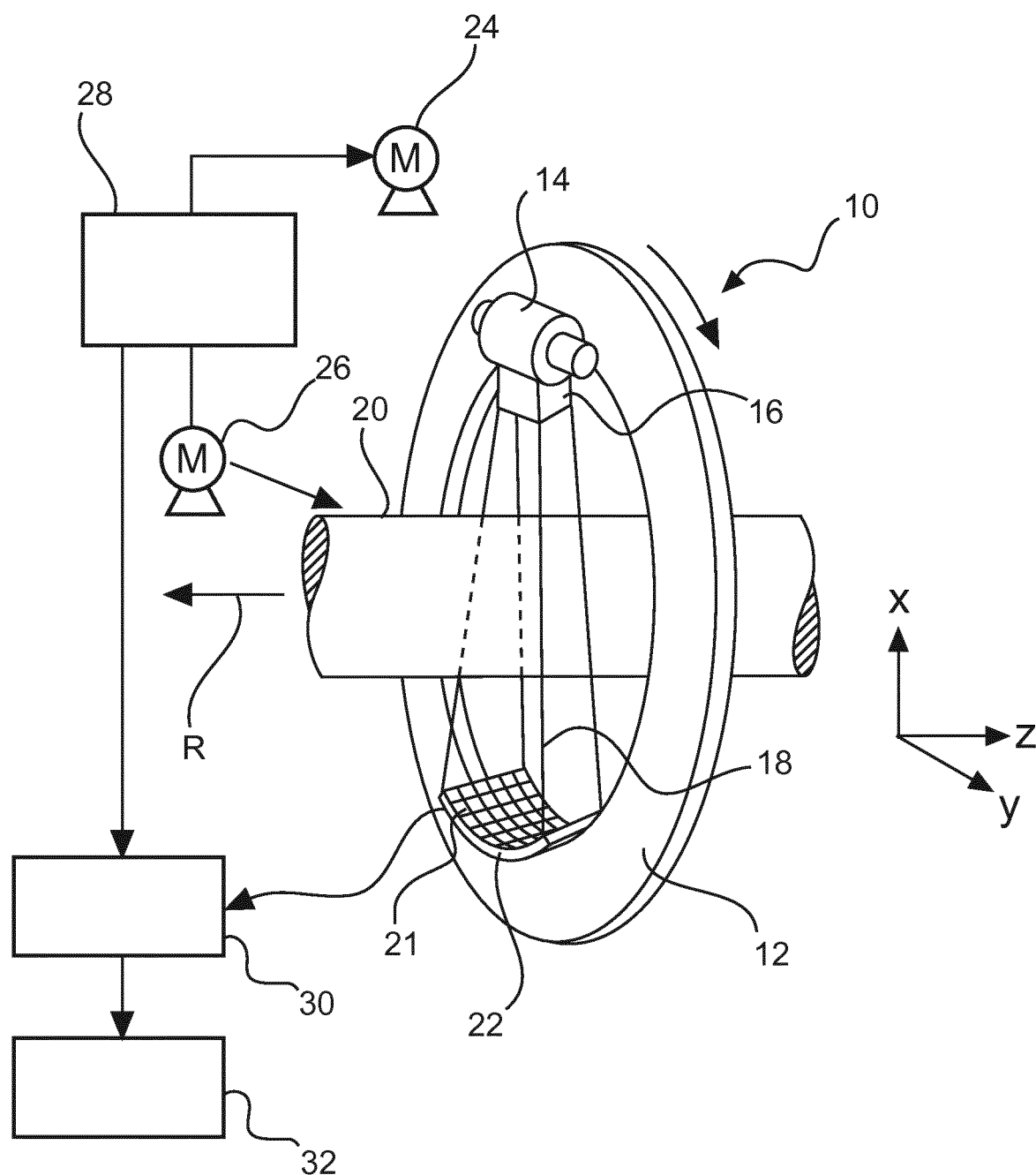
FIG. 1: a schematic illustration of an imaging system.

FIG. 1 shows schematically and exemplarily an imaging system 10 according to the present invention for imaging an object, in this example being a computed tomography (CT) apparatus. The CT apparatus 10 includes a gantry 12, which is capable of rotation about a rotational axis R, which extends parallel to a z direction. A radiation source 14 (also called photon source), which may be a polychromatic X-ray tube, is mounted on the gantry 12. The radiation source 14 is provided with a collimator 16, which forms a (e.g. conical) radiation beam 18 from the radiation (photons) generated by the radiation source 14. The radiation traverses an object of examination, such as a patient, arranged in an (e.g. cylindrical) imaging area 20 (also called examination zone).

After having traversed the imaging area 20, the radiation beam 18 is incident on a detection device for X-rays 22 (detector for detecting ionizing radiation), which comprises a two-dimensional detection surface. The detection device 22 is also mounted on the gantry 12. The detection device 22 comprises sensor(s) 21. The sensor(s) 21 provides a current in response to electromagnetic radiation exposure. The electromagnetic radiation is provided by radiation source 14. The detection device 22 comprises at least one capacitor and at least one photodiode coupled thereto. The photodiode can be equipped with a scintillator for the X-ray to optical conversion. A full cycle time is defined as the time that it takes to fully discharge the capacitor in response to the photodiode current signal provided by the sensor(s). The current also depends on whether the photodiode is common cathode or common anode. The invention is not restricted by the current sign (the only change required is the threshold by which the capacitor is recharged). This embodiment includes a common cathode, but it is not restricted thereto.

The CT apparatus 10 comprises two motors 24, 26. The gantry 12 is driven at a preferably constant but adjustable angular speed by the motor 24. The motor 26 is provided for displacing the object, for example, a patient, who is arranged on a patient table in the imaging area 20, parallel to the direction of the rotational axis R or the z axis. These motors 24, 26 are controlled by a control unit 28, for instance, such that the radiation source 14, the (detector) detection device 22 and the imaging area 20 move relative to each other along a helical directory. However, it is also possible that the object is not moved, but that only the radiation source 14 and the detector 22 are rotated, i.e. that the radiation source 14 moves along a circular trajectory relative to the object or the imaging area 20. Furthermore, in another embodiment, the collimator 16 can be adapted for forming another beam shape, in particular a fan beam, and the detector 22 can comprise a detection surface, which is shaped corresponding to the other beam shape, in particular to the fan beam.

During a relative movement of the radiation source 14 and the imaging area 20, the sensor(s) 21 provides a current in response to the electromagnetic radiation exposure (the provided current can be also called detection signals or detection values; preferably one signal value per pixel, i.e. per sensor or detection element). The signals are evaluated in readout electronics that may be included in the detector 22. The processor unit 30 is configured to provide a cycle time of at least one cycle, store the provided cycle time of the at least one cycle; and compare the cycle time of the at least one cycle with one or more previously stored cycle time(s). An estimate of an incomplete cycle is acquired prior to a change or interruption in a beam of the electromagnetic radiation or in an intensity of the electromagnetic radiation. The image reconstructed by the processor unit 30 may be provided to a display unit 32 for displaying the reconstructed image. The control unit 28 is preferentially also adapted to control the radiation source 14, the detection device 22 and the processor unit 30.

A direct converting detector can also be used according to a further embodiment. It usually comprises a directly converting semiconductor layer, e.g. cadmium telluride or CZT (cadmium-zinc-telluride), or Silicon(Si), GaAs, . . . . In this layer, charge carriers, i.e. particles carrying an electric charge such as electrons and holes are produced in response to incident ionizing radiation. By means of an electric field between an anode and a cathode, the charge carriers are detected via a plurality of electrodes. In other words, an incident photon (e.g. an x-ray photon) generates a charge carrier or a cloud of charge carriers upon incidence in the layer. By evaluating the number of charge carriers detected at the different electrodes it becomes possible to obtain a reading of the spatial location of the incident radiation in the directly converting semiconductor layer. Therefrom, an image of an object in the imaging area can be derived.

Figure 2:
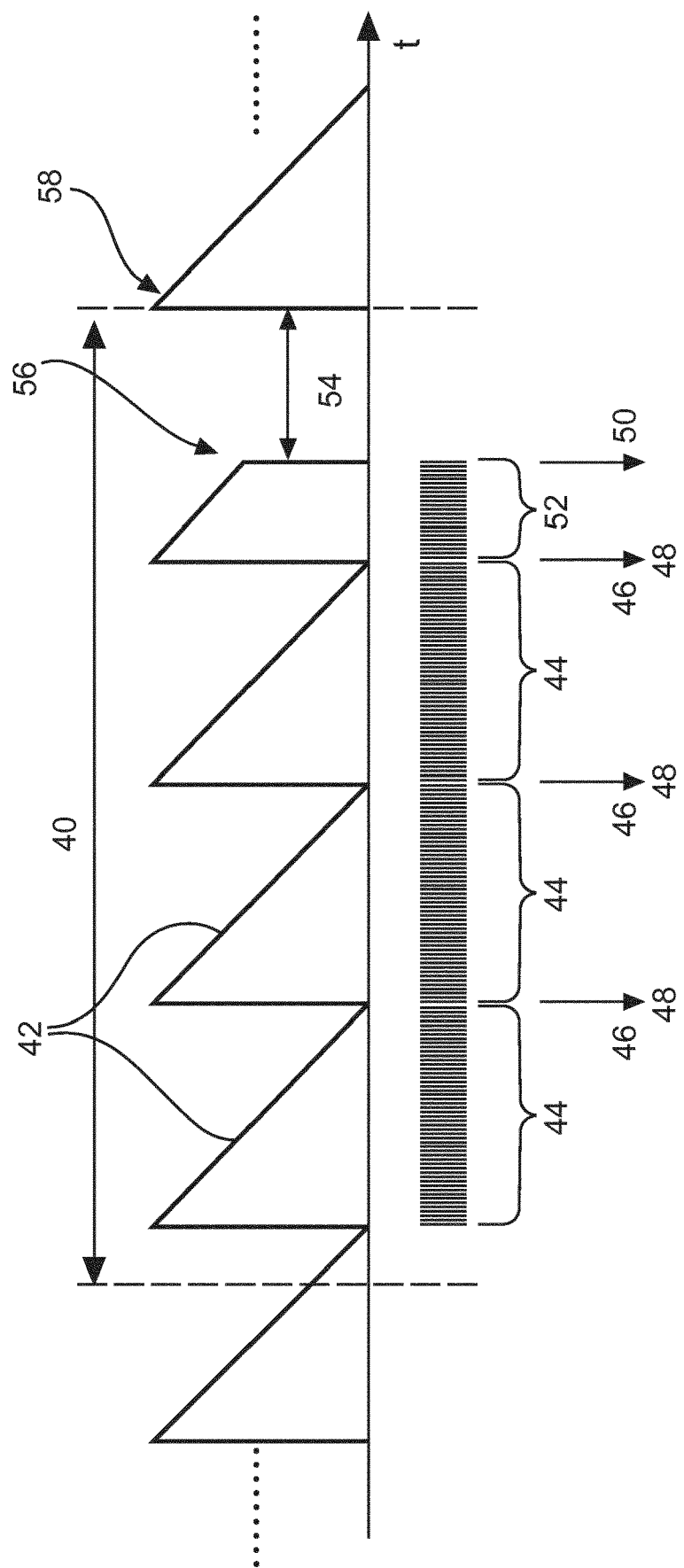
FIG. 2: a schematic illustration of a time diagram.

FIG. 2 shows a schematic illustration of a time diagram according to the invention. The time diagram showcases the functionality proposed by the invention. The integrator output (vertical axis) is shown as a function of time (horizontal axis). The integrator output is a voltage ramp 42 with a slope proportional to the input current provided by the sensor(s) 21 of the detection device 22. The integrator comprises a capacitor. When the integrator output reaches a threshold (which can be defined) a present amount of charge of the capacitor is discharged. The discharge of the capacitor causes a new cycle 46 in response to the current provided by the sensor.

Within an image frame 40, which can also be referred to as projection, the amount of charge of the capacitor is discharged during several cycles 46. The cycle time 44, the time that each cycle 46 takes, is measured. At the end of each cycle 46, the time is stored 48 and a new measurement is taken. If the subsequent cycle 46 is fully completed, i.e. full cycle time 44 is measured, a previous stored cycle time 44 is replaced by the actual cycle time 44 In this case, the last full cycle time 44 is stored.

However, also all cycle times 44 are stored and are provided for determining a variance of the cycle time 44 within an image acquisition frame 40 or within a plurality of image acquisition frames. Such variance is identified as variance of the cycle time 44 of all events.

If a cycle 46 is interrupted 50 before its completion, the time elapsed 52 until that moment is compared (ratio) to the cycle time 44 stored for the last completed cycle. The ratio between both cycle times represents an estimate of the incomplete cycle integrated over that capacitor before a discontinuity 54 of the electromagnetic radiation.

In this embodiment the discontinuity 54 is a blank period after a grid-switch event. The capacitor is reset and kept reset, so that an integrator output of a bias current, leakage current or the like is prevented while the X-ray source is switched off. At the end of the discontinuity 54 the capacitor reset is released and the next cycle 46 starts from known initial conditions, i.e. without any discontinuity. This is shown as integrator output 58.

For image acquisition methods such as kVp-switching or Grid-filter (both for dual-energy Spectral CT) upon a known change in intensity of the electromagnetic radiation (e.g. kVp switch or Dual focal spot (DFS) change), an estimate of an incomplete cycle is acquired prior to the intensity change as explained above. The proposed method can therefore be combined in one single implementation that covers Sparse sampling, kVp-switching, grid switching and Grid-based Spectral CT.

Measuring a cycle time can be done by a counter. The cycle time is defined as a period between a start of a new cycle and a full discharge of the capacitor based on the full-discharge signal provided to the counter by the capacitor discharge analyzer. The counter is preferably running at a high frequency. A counter frequency in the range of 50 MHz or above can be used.

Figure 3:
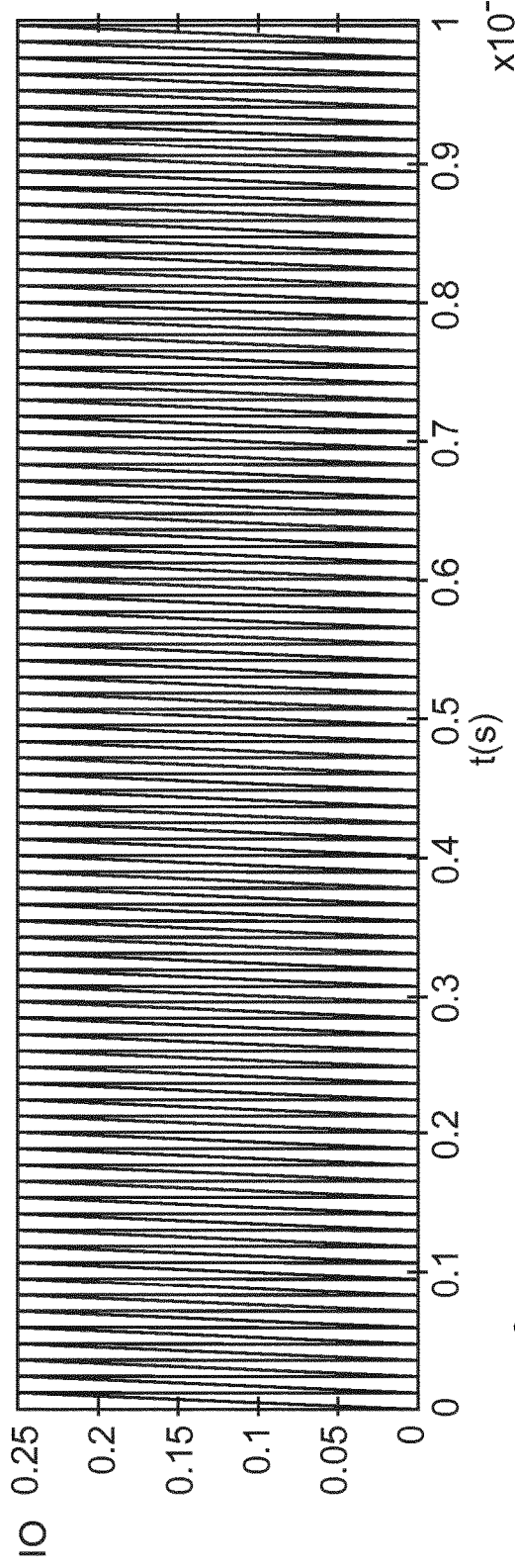
FIG. 3: an exemplary integrator output.

FIG. 3 shows an exemplary measured integrator output IO versus time t measured in seconds. In the shown embodiment the cycles (cf. cycles 46 in FIG. 2) are obtained for a realistic measurement by employing a fast scintillator (exemplary LaBr) and fast photodiode. The measurement includes Poisson inter-arrival times of impinging photons corresponding to a polychromatic 120 kVp spectrum.

Figure 4:
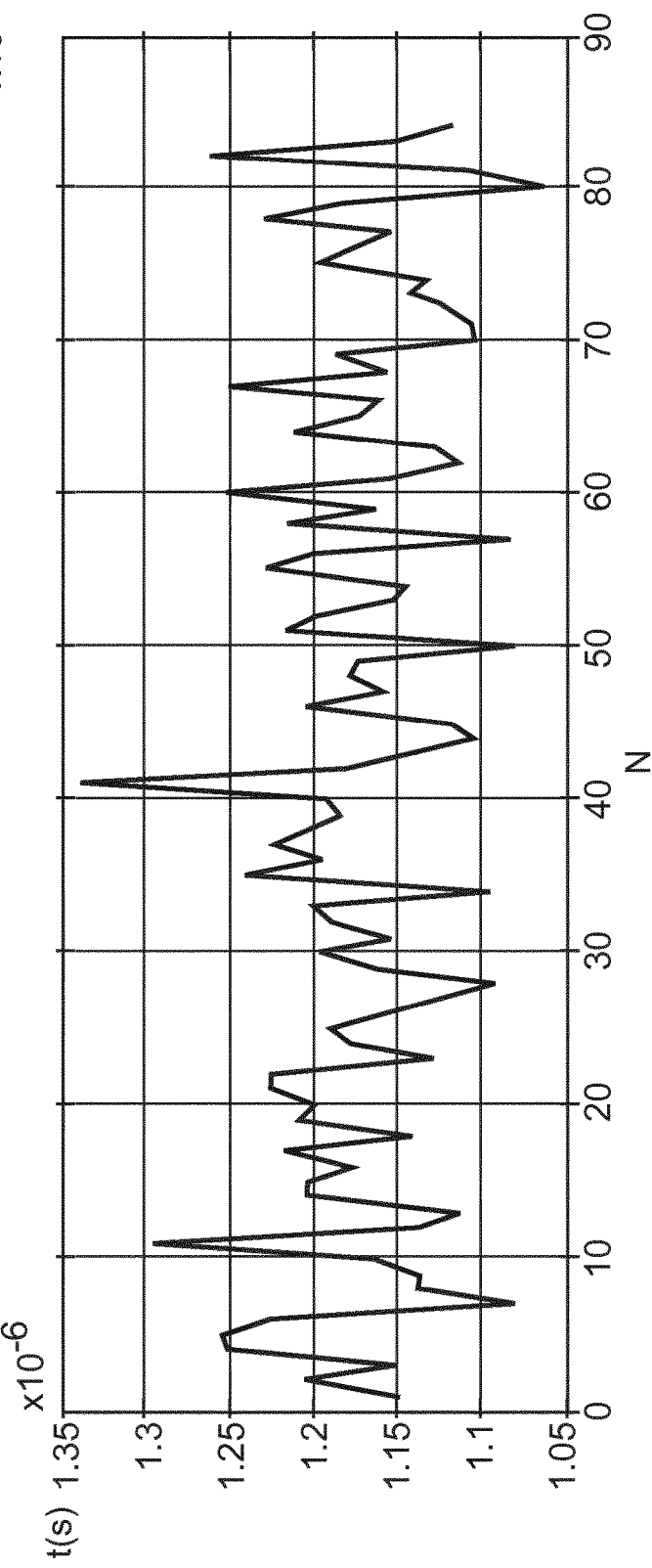
FIG. 4: a measured time cycles across all cycles of FIG. 3.

FIG. 4 shows the measured cycle time t on the vertical axis in seconds (cf. cycle time 44 in FIG. 2) for a number of N cycles 44 within the image acquisition frame shown in FIG. 3. This corresponds to a variance of the signal current of about 8e−17 in this example.

Figure 5:
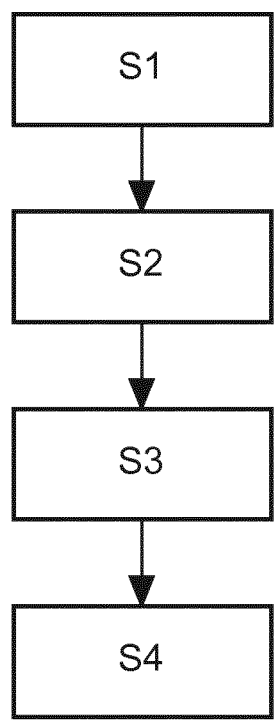
FIG. 5: a flow chart according to the method of the invention.

FIG. 5 shows a flow chart according to the method of the invention. Step S1 provides sensing electromagnetic radiation exposure during at least one image acquisition frame. A cycle time of at least one cycle is provided S2. The cycle time of the at least one event is stored S3. The cycle time of the at least one event is evaluated S4 wherein an estimate of an incomplete cycle is acquired prior to a discontinuity of the electromagnetic radiation, wherein the discontinuity is a change or interruption in a beam of the electromagnetic radiation or in an intensity of the electromagnetic radiation. A default value DV is provided before the storing of the first cycle time.

Figure 6:
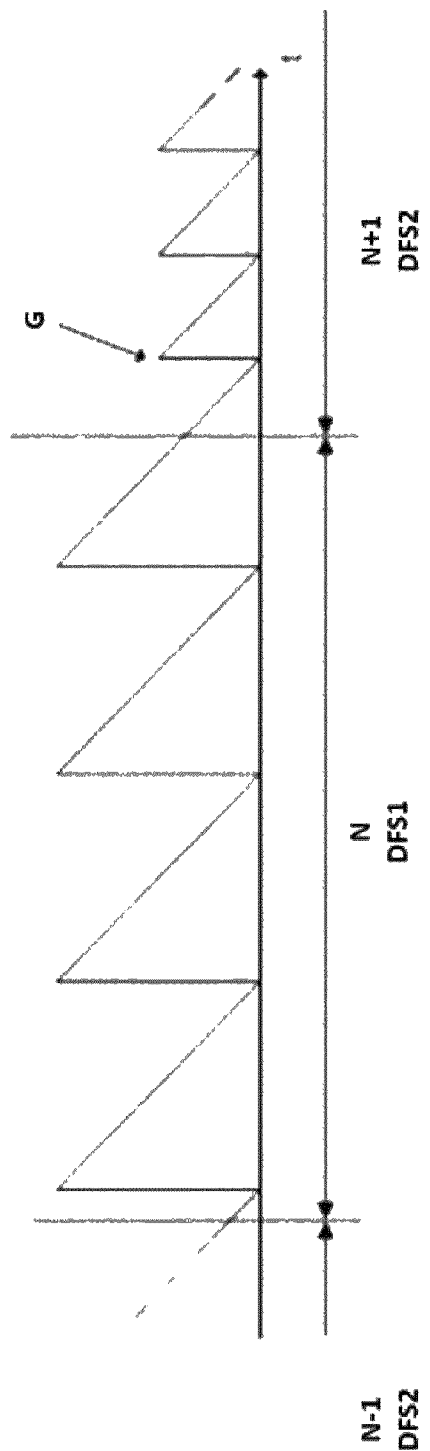
FIG. 6: another schematic illustration of a time diagram.

FIG. 6 shows another schematic illustration of a time diagram exemplary of a current-to-frequency type of circuit. The integrator output (vertical axis) is shown as a function of time (horizontal axis).

A discontinuity in an intensity of the electromagnetic radiation might occur, e.g. when using of a fine-pitch grid in front of the X-ray tube (source) and making use of a focal spot deflection (DFS). Such discontinuity is compensated by a gain modification in the shown example.

In a current image acquisition frame N, a first position DFS1 of the focal spot is provided. The previous acquisition frame N−1 and the following acquisition frame N+1 provides an alternate position DFS2 of the focal spot.

For each image acquisition frame N−1, N, N+1 the gain is modified by adding a reference voltage. In this example, the reference voltage is automatically switched for each image acquisition frame synchronous with the trigger for the image acquisition frame. The effective change of the gain G only takes place upon the first cycle in the image acquisition frame of the following frame N+1 in this example.

As it can be seen in FIG. 6, the change of gain implies that an offset frequency is also affected by the same gain. Although not strictly necessary, also the bias current can be changed by the same ratio as the reference voltages. This allows to adapt the current (reduce the bias) for the higher gain region and thereby reducing the noise induced by an unnecessarily large current. This might be particularly required, if the frame times are not kept the same, i.e. in the event of having image acquisition frames with the alternate position DFS2 of the focal spot longer than image acquisition frames with the first position DFS1 of the focal spot. In other examples the DFS positions may relate to different kVp settings in e-g-kVp-switching.

The gain changes described above are coherent with the known change of beam quality which is expected from kVp-switching or DFS applications. The gain change has been illustrated in the form of a current-to-frequency type of readout circuit. Other circuits (e.g. gain amplifier) can be equally adapted to respond to known changes in tube beam quality by changing the operating settings accordingly.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A detection device for X-rays, comprising:
   at least one sensor configured to provide a current in response to electromagnetic radiation exposure during at least one image acquisition frame;
   at least one electronics board comprising at least one integrator providing a capacitor that is configured to discharge in response to the current provided by the sensor, wherein a discharge of the capacitor defines at least one cycle;
   a capacitor discharge analyzer configured to analyze the discharge of the capacitor and to provide a full-discharge signal when the capacitor is fully discharged in response to the current provided by the sensor;
   a counter configured to measure a cycle time, defined as a period between a start of a new cycle and a full discharge of the capacitor based on the full-discharge signal provided to the counter by the capacitor discharge analyzer; and
   a processor configured to:
     obtain the cycle time of the at least one cycle from the counter;
     store the obtained cycle time of the at least one cycle;
     compare the cycle time of the at least one cycle with one or more previously stored cycle times; and
     provide an estimate of an incomplete cycle acquired prior to a discontinuity of the electromagnetic radiation, wherein the discontinuity is a change or interruption in a beam of the electromagnetic radiation or in an intensity of the electromagnetic radiation.

2. A method for detecting electromagnetic radiation comprising:
   sensing electromagnetic radiation exposure during at least one image acquisition frame;
   providing a cycle time of at least one cycle, wherein the cycle time is defined as the period to fully discharge a capacitor of at least one integrator of an electronics board of the detection device;
   storing the provided cycle time of the at least one cycle; and
   comparing the cycle time of the at least one cycle with one or more previously stored cycle times; wherein an estimate of an incomplete cycle is acquired prior to a discontinuity of the electromagnetic radiation, wherein the discontinuity is a change or interruption in a beam of the electromagnetic radiation or in an intensity of the electromagnetic radiation.

3. The method according to claim 2, wherein the cycle time of the at least one cycle replaces the stored cycle time of a last completed cycle; if the at least one cycle is complete.

4. The method according to claim 2, wherein the estimate for the incomplete cycle is acquired for a cycle time which is less than the stored cycle time of the last completed cycle.

5. The method according to claim 2, wherein the ratio of the provided cycle time and the cycle time for the last completed cycle represents an estimate of the incomplete cycle.

6. The method according to claim 2, wherein the cycle times of all cycles during at least one image acquisition frame are provided and a variance of the cycle time is calculated.

7. The method according to claim 2, wherein the discontinuity comprises at least one of a change of wavelength of the electromagnetic radiation, a blank period of the electromagnetic radiation, and a change.

8. The method according to claim 2, wherein a discontinuity of the electromagnetic radiation is compensated by modifying a gain of the at least one cycle during the at least one image acquisition frame.

9. The method according to claim 8, wherein the modification of the gain comprises adding a reference voltage which resets the capacitor when the signal reaches a certain threshold.

10. The method according to claim 8, wherein the reference voltage is different for subsequent image acquisition frames.

11. A non-transitory computer-readable medium having executable instructions stored thereon which, when executed by at least one processor, cause the at least one processor to perform a method for detecting electromagnetic radiation, the method comprising:

sensing electromagnetic radiation exposure during at least one image acquisition frame;

providing a cycle time of at least one cycle, wherein the cycle time is defined as the period to fully discharge a capacitor of at least one integrator of an electronics board of the detection device;

storing the provided cycle time of the at least one cycle; and comparing the cycle time of the at least one cycle with one or more previously stored cycle times;

wherein an estimate of an incomplete cycle is acquired prior to a discontinuity of the electromagnetic radiation, wherein the discontinuity is a change or interruption in a beam of the electromagnetic radiation or in an intensity of the electromagnetic radiation.

* * * * *